United States Patent [19]

Taniguchi et al.

[11] 4,320,378
[45] Mar. 16, 1982

[54] OXYGEN SENSOR

[75] Inventors: Harutaka Taniguchi; Kenichi Hara; Hideo Shiraishi; Shinji Kiyofuji, all of Kawasaki, Japan

[73] Assignee: Fuji Electric Co. Ltd., Kanagawa, Japan

[21] Appl. No.: 194,248

[22] PCT Filed: Jul. 26, 1979

[86] PCT No.: PCT/JP79/00196

§ 371 Date: Mar. 18, 1980

§ 102(e) Date: Mar. 18, 1980

[87] PCT Pub. No.: WO80/00373

PCT Pub. Date: Mar. 6, 1980

[30] Foreign Application Priority Data

Jul. 26, 1978 [JP] Japan .................................. 53-91204

[51] Int. Cl.³ ............................................. H01L 7/00
[52] U.S. Cl. .................................... 338/34; 73/27 R; 338/229; 338/271; 422/98
[58] Field of Search ................... 338/34, 13, 271, 229, 338/28, 30; 73/27 R; 422/98; 23/232 E; 324/65 R, 65 P

[56] References Cited

U.S. PATENT DOCUMENTS 4,007,435 2/1977 Tien ...................................... 338/34
4,130,797 12/1978 Hattori et al. .................... 338/34 X
4,206,173 6/1980 Yamaguchi et al. ............. 338/34 X

FOREIGN PATENT DOCUMENTS 48-70596 9/1973 Japan .
48-90294 11/1973 Japan .
49-60785 6/1974 Japan .
50-51787 5/1975 Japan .
52-95294 8/1977 Japan .

Primary Examiner—C. L. Albritton

[57] ABSTRACT

Into a metal tube (24) provided with vent-holes (32) is inserted an oxygen sensor element (10) which comprises a ceramic round rod coated with a porous thick membrane of transition-metal oxide, divided electrode thick membranes (14) and a protective layer therefor, thereby to obtain an oxygen sensor. One electrode of the oxygen sensor element is connected to the metal tube and the opposite electrode is connected to a connecting lead wire (64, 66) electrically insulated from the tube, so that the oxygen sensor is rich in toughness against the mechanical oscillation and impact. The sensor may suitably be used to detect the oxygen content in the waste gas of automobiles.

5 Claims, 4 Drawing Figures

OXYGEN SENSOR

TECHNICAL FIELD

This invention relates to an oxygen sensor for detecting oxygen content in a waste gas from automobiles or the like which has superior mechanical toughness and sensitivity and comprises a metal tube having vent holes and a ceramic round rod inserted therein and including a thick membrane of transition-metal oxide, electrode thick membranes divided into two parts and a protective layer covering the membranes wherein one electrode thick membrane is connected to the metal tube whereas the opposite thick membrane is connected to a connecting lead wire electrically insulated from the tube.

BACKGROUND OF THE INVENTION

As one convenient measure for public nuisance of the waste gas exhausted from a heat engine such as an automobile internal engine, a tertiary catalyst system has been suitably employed to clear up at once the desired regulations of nitrogen oxides ($NO_x$), carbon monooxide (CO) and hydrocarbons. In the tertiary catalyst system, the characteristics of the tertiary catalyst may not have effective function unless an air/fuel ratio (A/F ratio) is controlled in a very narrow range of equivalent ratio or a theoretical air/fuel ratio. The A/F ratio is conveniently controlled in such a way that the oxygen content after combustion is measured by the oxygen sensor as a change in the oxygen partial pressure and the measured signal is fed back to the control system of the electronic fuel injection pump for example. To measure the change in the oxygen partial pressure, various types of oxygen sensors have been developed employing the transition-metal oxide in which the electric resistance is varied depending on the oxygen concentration.

The oxygen sensor of this type may be prepared by mixing for example titanium dioxide material powder with suitable solvent, binder, plasticizer, dispersant and the like forming a green sheet by the doctor blade technique for subsequent lamination with a platinum electrode and a heater under the pressure with dryness and then sintering the resultant product to form a porous disc. This process is disclosed in the opened Japanese Patent application No. 50-56292. In order to actually mount this element for an exhaust tube of the automobile, a platinum lead wire is lead out through a passage provided in a ceramic body fixed to a metal housing with a possible seal preventing the gas leakage from the sensor element to the atmosphere. The actual layout of such the element is technically disclosed in the opened Japanese Utility Model Applications No. 52-46781 and No. 52-4792.

However, the structure of the known element is relatively inferior in strength with such the disadvantage that a boundary part of the lead wire prolonged from the element becomes weak against oscillation and impact. Further, the prolonged platinum wire necessitates a passage to be formed as a groove or hole in the ceramic with relatively the high cost in production and difficulty in sealing for the gas leakage.

DISCLOSURE OF THE INVENTION

An object of the invention is to solve the problems of the disc type oxygen sensor by inserting into a metal tube a ceramic round rod comprising a thick membrane of transition-metal oxide, electrode thick membranes and a protective layer therefor and also to provide an oxygen sensor which is superior in the mechanical strength, durability and economy. This object may be achieved in accordance with the invention in such a way that into a metal tube having a closed end and vent holes in its side wall is inserted a ceramic round rod which includes on its surface a thick membrane of transition-metal oxide, electrode thick membranes made into contact with the thick membrane and divided into two parts and a protective layer covering whole the thick membrane of transition-metal oxide and at least part of electrode thick membranes and one of the electrode thick membranes divided into two parts is connected to a bottom of the tube whereas the opposite electrode thick membrane is connected to a connecting lead wire extended from an open end of the tube in insulation from the tube. The oxygen sensor thus concentrated has an improved mechanical toughness with simple structure and sufficiently resistive to the oscillation and impact and may be manufactured at a low cost.

BRIEF DESCRIPTION OF THE DRAWINGS

The drawings illustrate the preferred embodiments of the oxygen sensor according to the invention, wherein.

BEST MODE FOR CARRYING OUT THE INVENTION

Figure 1:
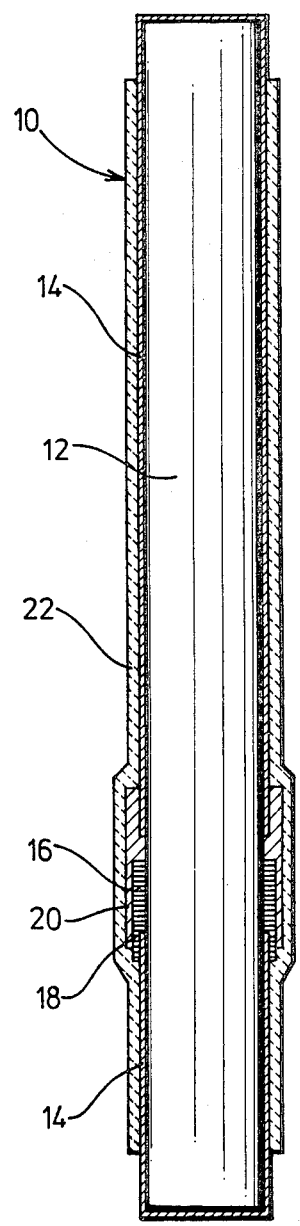
FIG. 1 is a longitudinally sectioned view of one embodiment of the oxygen sensor element according to the invention.

In FIG. 1, the reference numeral 10 represents an element used in an oxygen sensor according to the invention. A round rod base body 12 of aluminum oxide ($Al_2O_3$) constituting the element 10 is primarily printed with a platinum electrode thick membrane 14 as a first layer by a screen printing method and then subjected to a firing. As will be readily appreciated from the accompanying drawing, the platinum electrode thick membrane 14 is divided into two parts to provide a distance 16 on the base 12 and the divided platinum electrode thick membranes 14 cover respectively the surface of the round rod 12 including opposite ends. Then, a titanium dioxide thick membrane 18 is printed by the screen printing method to fill the distance 16 leaving a part and to cover a part of one platinum electrode thick membrane 14 with a thickness of 50 to 100 μm after firing. After dryness of the titanium dioxide thick membrane 18, a second layer of the platinum electrode thick membrane 20 is printed to fill the left part of the distance 16 and cover the most part of the titanium dioxide thick membrane 18 contacting with one of the platinum electrode thick membranes 14. These platinum electrode thick membranes 20 and the titanium dioxide thick membrane 18 are simultaneously fired at an elevated temperature. Therefore, Mg O.$Al_2O_3$ ceramic 22 is sprayed by means of a plasma spray coating apparatus to coat the titanium dioxide thick membrane 18, all the platinum electrode thick membranes 20 and the most part of the platinum electrode thick membrane 14 formed as the first layer. The thickness of the sprayed membrane is determined in the range of 50 to 100 μm with rich porosity.

Figure 3:
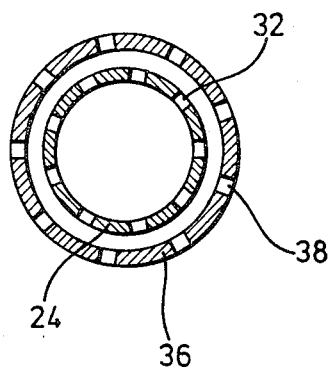
FIG. 3 is a cross sectioned view of a double wall portion of a metal tube housing constituting the oxygen sensor and FIG. 4 is a cross sectioned view of the double wall portion of the metal tube housing of another embodiment.
Figure 4:
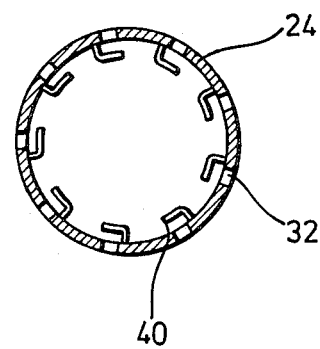
Figure 2:
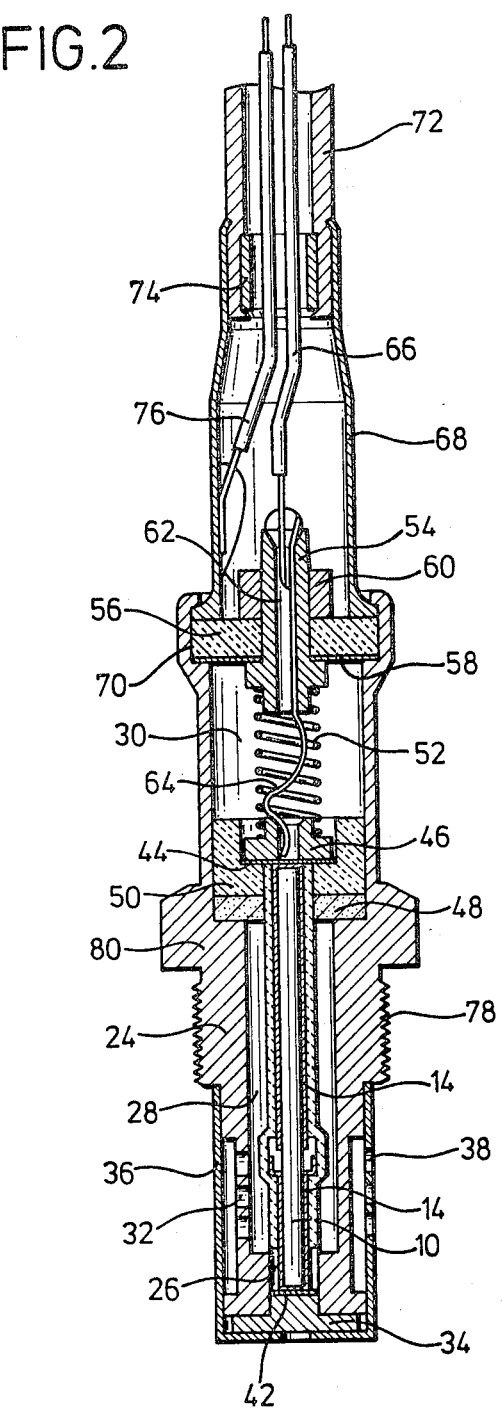
FIG. 2 is a longitudinally sectioned view of the oxygen sensor incorporated with the element of FIG. 1.

FIG. 2 shows a structure of the oxygen sensor accommodating therein an oxygen sensor element of the construction as hereinbefore described. The oxygen sensor provides a metal housing 24 of stainless steel or thermal resistant alloy in which the cylindrical spaces 26, 28 and 30 with inner diameters increasing seriatim are formed. In the side wall of the housing 24, near the cylindrical space 26 is arranged openings 32 which communicates to the cylindrical space 28. The openings 32 are arranged in three rows at equal distances spaced apart each other on the same circumference and in a vertical direction, thus totaling to 27 openings as shown in FIG. 3. To one open end of the metal housing 24 is mounted a first contacting terminal 34 having a flange which is engaged with the end of the housing. The first contacting terminal 34 and the end of the metal housing 24 are encased by a metal cover 36. Namely, the first contacting terminal 34 is embraced between the end of the metal housing 24 and the metal cover 36. The opening portion 32 of the metal housing 24 are formed in relatively thin thickness, so that the metal cover 36 and the side wall provided with the openings 32 form double walls spaced apart each other at a given distance. In the wall of the opposite metal cover 36 are formed total twenty seven openings 38 like the opening 32. The waste gas is introduced through the openings 38 into a detecting part of the element 10. The openings 38 are arranged so as not to align with the openings 32 to avoid the direct contact of noncombusted portion of the waste gas, impure metal pieces or pressure pulses with the element 10 as shown in FIG. 3. In order to perform the same subject, the wall opening 32 of the housing 24 may be formed as illustrated in FIG. 4, in lieu of providing the double walls. Namely, plates 40 may be arranged within the housing 24 at the positions corresponding to the openings 32. One end of the detecting element 10 is inserted into the cylindrical space 26 and the platinum thick membrane 14 at its one end is made into contacted with the first contacting terminal 34 through a platinum foil 42 of not more than 0.5 mm. The detecting element 10 at its opposite end is protruded into the cylindrical space 30 and the platinum thick membrane 14 of the end surface is similarly made into contact with a second contacting terminal 46 through a platinum foil 44. The second contacting terminal 46 is carried on the end of the cylindrical space 30 through a ceramic wool ring 48 and an insulating collar 50. A compression spring 52 is engaged with a flanged portion of the second contacting terminal 46, so that the pressing contact takes place between the ends of the element 10 and the first and second contacting terminals 34, 46. The platinum foils 42 and 44 serve to reducing the contact resistance between the ends of the element 10 and the contacting terminals 34, 46, although the platinum in place of the platinum foils may be applied to the surfaces of the contacting terminals by the convenient plating or spattering method. The ceramic wool ring 48 has the functions of cushioning the compression spring 52 and of insulating the heat of the waste gas transmitted from the cylindrical space 28. The opposite end of the compression spring 52 is supported on a flanged portion of the contacting terminal 54 which is in turn fixed by mounting through an asbestos packing 58 to an insulating collar 56 supported on the metal housing 24 and also mounting a metal collar 60 to the insulating collar 56.

The contacting terminal 54 is provided along its central axis with a hole 62 into which are inserted a heat-resistent lead wire 64 and a lead wire 66. A heat resisting lead wire 64 at its one end is brazed to the second contacting terminal 46 at the high temperature or with a hard solder, whereas the opposite end thereof is brazed together with the lead wire 66 to the open end of the contacting terminal 54 at the high temperature or with the hard solder thereby to seal the hole 62. The insulating collar 56 and the asbestos packing 58 with a metal sheath 68 forming an extended part of the metal housing 24, are accommodated in the internal space 70 in engagement with the opening end of the housing 24.

Into the opposite end of the metal sheath 68 are inserted, a heat-resistent tube 72 made from silicone rubber with a collar 74 and the end of the metal sheath 68 is calked for fixing. The heat resisting tube 72 accommodates the lead wire 66 and a lead wire 76 which at its one end is connected to the metal sheath 68 for protection of these lead wires as well as retardation of penetration of rain or salt water from the outside. The oxygen sensor thus constituted is fastened to an exhaust tube body through a packing by means of a thread 78 provided in the outer surface of the metal housing 24 with a bolt 80.

As hereinbefore fully described, the oxygen sensor according to the invention is mechanically simple and stable in structure with various advantage of preventing the gas leakage as well as the water penetration perfectly and improvements in the durability and the cost for manufacture.

INDUSTRIAL APPLICABILITY OF THE INVENTION

As hereinbefore fully described, the oxygen sensor according to the invention has an improved durability even against mechanical stress with an excellent sensitivity so that it may be suitably used for controlling the waste gas exhausted from the heat engine, particularly from the automobile inner engine and also is preferably applicable to an analyzing sensor, a thermosensor or the like.

We claim:

1. An oxygen sensor for detecting a change of oxygen partial pressure in an ambient atmosphere through a change of electric resistance of transition-metal oxide, characterized in that a ceramic round rod (12) providing on its surface a thick membrane of transition-metal oxide (18), electrode thick membranes (14) divided into two parts in contact with said thick membrane (18) of transition-metal oxide and a protective layer (22) covering whole the thick membrane (18) of transition-metal oxide and at least part of electrode thick membranes (14) is inserted into a metal tube (24) having a closed end and holes (32) in its side wall and that one of said divided electrode thick membranes (14) is connected to a bottom of said metal tube (24) while the opposite electrode thick membrane (14) is connected to a connecting lead wire (66) which is drawn from an opening of the metal tube (24) in insulation from said metal tube (24).

2. An oxygen sensor as claimed in claim 1, wherein the metal tube (24) provides two walls with a metal cover and parts of side walls are spaced at a given distance and vent-holes (32) and (38) are provided in said walls so as not to align with each other.

3. An oxygen sensor as claimed in claim 1 or 2, wherein the divided electrode thick membranes (14) are extended respectively to the different end surfaces of the ceramic round rod (12), one electrode metal thick membrane (14) on said end surface is made under pressure into contact with a contacting terminal (34) in contact with a bottom of the metal tube (24), while the opposite electrode metal thick membrane (14) is made under pressure into contact with another contacting terminal (46) connected to a connecting lead wire (66).

4. An oxygen sensor as claimed in claim 3, wherein the contacting terminals (34) and (46) are coated with an anticorrosive and elastic metal.

5. An oxygen sensor as claimed in claim 4, wherein the coating metal consists of platinum.

* * * * *